(12) United States Patent
Tu

(10) Patent No.: US 9,440,847 B2
(45) Date of Patent: Sep. 13, 2016

(54) SINGLE SILICON WAFER MICROMACHINED THERMAL CONDUCTION SENSOR

(71) Applicant: Xiang Zheng Tu, San Jose, CA (US)

(72) Inventor: Xiang Zheng Tu, San Jose, CA (US)

(73) Assignee: POSiFA MICROSYSTEMS, INC., San Jose, CA (US)

( * ) Notice: Subject to any disclaimer, the term of this patent is extended or adjusted under 35 U.S.C. 154(b) by 85 days.

(21) Appl. No.: 14/045,555

(22) Filed: Oct. 3, 2013

(65) Prior Publication Data

US 2015/0097260 A1    Apr. 9, 2015

(51) Int. Cl.
*G01N 25/18* (2006.01)
*B81C 1/00* (2006.01)
*G01N 27/18* (2006.01)

(52) U.S. Cl.
CPC ............. *B81C 1/0069* (2013.01); *G01N 27/18* (2013.01); *B81B 2201/0214* (2013.01); *B81C 2201/0115* (2013.01)

(58) Field of Classification Search
CPC ...................................................... G01N 27/18
USPC .............................................. 374/31, 10, 33
See application file for complete search history.

(56) References Cited

U.S. PATENT DOCUMENTS

| | | | |
|---|---|---|---|
| 5,093,073 A * | 3/1992 | Schenker | 376/310 |
| 7,367,237 B2 * | 5/2008 | Hsiai et al. | 73/841 |
| 7,452,126 B2 * | 11/2008 | Arndt et al. | 374/44 |
| 2007/0209433 A1 * | 9/2007 | Gehman | G01F 1/692 73/204.26 |
| 2012/0126346 A1 * | 5/2012 | Hoechst | B81C 1/00595 257/416 |

OTHER PUBLICATIONS

Pollak-Diener, Gerhard and Obermeier, E. Sensors and Actuators B, 13-14. "Heat-conduction micro-sensor based on silicon technology for the analysis of two and three component gas mixtures". 1993 (345-347). Germany. Technical University of Berlin, Microsensor Technology.
Simon, Isolde and Arndt, Michael. Sensors and Actuators, A97-98. "Conductivity sensor for the detection of hydrogen in automotive application". 2002. (104-108). Reutlingen, Germany. Elsevier.
Udina, S. Sensors and Actuators B 134. "A micromachined thermoelectric sensor for natural gas analysis: Thermal model and experimental results". 2008. (551-558). Spain. Elsevier B.V.

* cited by examiner

*Primary Examiner* — Lisa Caputo
*Assistant Examiner* — Nasir U Ahmed
(74) *Attorney, Agent, or Firm* — James M. Wu; JW Law Group

(57) ABSTRACT

A single silicon wafer micromachined thermal conduction sensor is described. The sensor consists of a heat transfer cavity with a flat bottom and an arbitrary plane shape, which is created in a silicon substrate. A heated resistor with a temperature dependence resistance is deposed on a thin film bridge, which is the top of the cavity. A heat sink is the flat bottom of the cavity and parallel to the bridge completely. The heat transfer from the heated resistor to the heat sink is modulated by the change of the thermal conductivity of the gas or gas mixture filled in the cavity. This change can be measured to determine the composition concentration of the gas mixture or the pressure of the air in a vacuum system.

8 Claims, 4 Drawing Sheets

FIG. 7B A-A
Cross-Section of FIG. 7

B-B Cross-Section of FIG. 7

SINGLE SILICON WAFER MICROMACHINED THERMAL CONDUCTION SENSOR

FIELD

The invention relates to a thermal conduction sensor. Particularly, the invention relates to a single silicon wafer micromachined thermal conduction sensor consisting of a heat transfer cavity having a flat bottom and an arbitrary plane shape, which are all created in a silicon substrate and in which no gas natural convection takes place and the heat transfer is through the thermal conduction of the gas filled in the cavity.

BACKGROUND

Gas sensors have been in use for several decades. The principle of most current gas sensors relies on chemical interactions between the gas and a specific material which provides high sensitivity. It is well known that such chemical sensors suffer from poor stability over time, due to involving chemical reactions. In order to circumvent this problem thermal conduction sensors that make use of the physical properties of gases, have been developed.

Thermal conductivity measurement has been used in gas chromatography for more than 100 years, this gas detection method is still of large importance in process control and gas analysis. Furthermore, it presently experiences a revival due to the progress in silicon micromechanical electrical system (MEMS). A MEMS thermal conduction sensor allows a high degree of integration and miniaturization. Power consumption, response time and production costs of thermal conduction sensors can thus be dramatically reduced.

Ideally, the MEMS thermal conduction sensor consists of a heated resistor, a heat sink and a gas cavity. The heated resistor is located on a thin film bridge and thus thermally insulated against a supporting substrate. The gas cavity is located between the heat source and the heat sink. When a MEMS thermal conduction sensor is in operation, heat transfers from the heat source to the heat sink. Any change in the gas concentration, and thus the thermal conductivity of the gas cavity, results in a change in the bridge temperature. This change in temperature is measured with a temperature sensor, which is also located on the thin film bridge and is thermally linked very closely to the heated resistor.

Gerhard Pollak-Diener and E. Obermeier presented a micromachined thermal sensor which is suitable for the analysis of binary and ternary gas mixtures. Both the heat source and heat sink of the sensor are made of silicon. A first silicon wafer is etched in hot potassium hydroxide in order to produce a thin film bridge for carrying a heated resistor. A second silicon wafer is etched to form a cavity and used as a heat sink. The second silicon wafer is mounted above the first silicon wafer. The first silicon wafer is supported on the back side by an insulated wafer. (Heat-conduction microsensor based on silicon technology for the analysis of two- and three-component gas mixtures, Sensors and Actuators B, 13-14 (1993) 345-347).

Arndt Michael and Lorenz Gerd revealed a thermal conduction sensor including a thermally insulated diaphragm formed by a recess in a base plate exhibiting poor thermal conductivity. On one or both sides, the diaphragm is covered by a porous cover plate permitting gas exchange by diffusion, a cavity being left open between the diaphragm and the porous cover plate. (U.S. Pat. No. 7,452,126, Arndt, et al., Nov. 18, 2008).

Several disadvantages can be found in the above first design. In the sensor fabrication process two silicon wafers are first processed individually. Then the wafers are bonded together through a wafer-level bonding process. Finally, the stack of the bonded wafer is mounted on the surface of a insulate wafer. Such complicated and cumbersome process is far from efficient and economical.

In the above second design the fabrication process also consists of wafer-level bonding. Furthermore, the silicon wafer is required to bond to a particular silicon carbine plate or an aluminum oxide plate instead of a commonly used silicon wafer or a glass wafer.

In 2002 year, Isolde Simon and Michael Arndt reported a micromachined conductivity sensor for hydrogen detection. A "hot" element of the sensor is realized as a platinum heat source structure on a thin film silicon-nitride dielectric bridge. A "cold" element is formed by the bulk silicon surrounding the bridge and by the gas surrounding the sensor. (Conductivity sensor for the detection of hydrogen in automotive application, Sensors and Actuators, A97-98 (2002) 104-108)

In 2008 year, S. Udina et al described a thermal conduction sensor for natural gas analysis. The sensor structure consists of a thin film bridge defined on a silicon chip. The bridge is a multilayer sandwich structure of silicon dioxide/silicon nitride and used as a hotplate. A polysilicon heat source is located in the hotplate and a boron-doped silicon island is located right below as a thermal spreader for better temperature homogeneity across the hotplate. The backside of the die is attached to a metal casing (TO-8) acting as a heat sink to keep the substrate temperature approximately constant. The TO-8 casing presents a drilled hole in the area right below the bridge, which improves gas exchange with the surrounding atmosphere. (A micromachined thermoelectric sensor for natural gas analysis: Thermal model and experimental results, Sensors and Actuators B 134 (2008) 551-558).

In the above two design the heat generated by heat source flows through the surrounding gas instead of a gas cavity. In an open space it is impossible to limit the heat transfer to be conduction, because the Rayleigh number may be much higher than a critical number for natural convection to occur. The temperature behavior of the heater depends on both conduction and natural convection, experimental data exploitation will be quite tricky and difficult to analyze.

SUMMARY

In view of the above related arts, the present invention provides a micromachined thermal conduction sensor having the following features.

One feature of the micromachined thermal conduction sensor provided by the present invention is that the sensor has a heat transfer cavity consisting of a cavity, a thin film bridge carrying a heated resistor and a bottom used as a heat sink, which are all created in a silicon substrate such that wafer level bonding (is a packaging technology on wafer-level for the fabrication of microelectromechanical systems (MEMS)) is not required.

Another feature of the micromachined thermal conduction sensor provided by the present invention is that the cavity has a Grashof number (Gr is a dimensionless number in fluid dynamics and heat transfer which approximates the ratio of the buoyancy to viscous force acting on a fluid) is less than $1 \times 10^{-2}$ such that no natural convection takes place completely in the cavity.

Still another feature of the micromachined thermal conduction sensor provided by the present invention is that the bottom of the cavity is flat and the gap between the thin film bridge and the bottom is uniform and consistency along the bottom.

Still another feature of the micromachined thermal conduction sensor provided by the present invention is that the thickness of the thin film bridge is much less than the length of the bridge, which is beneficial for the heat transfer from the heated resistor to the heat sink.

Still another feature of the micromachined thermal conduction sensor provided by the present invention is that the heated area by the heated resistor is less than the area of the thin film bridge, which is beneficial for the heat transfer from the heated resistor to the heat sink.

Still another feature of the micromachined thermal conduction sensor provided by the present invention is that the most fabrication processes of the sensor can be carried out in a stander COM production line, in which there are no wafer level bonding and double side alignment available.

Still another feature of the micromachined thermal conduction sensor provided by the present invention is that the release of the microstructure of the heat transfer cavity can be done at the final step of the fabrication process.

Still another feature of the micromachined thermal conduction sensor provided by the present invention is that without any changes the sensor can be used as a vacuum sensor and a humidity sensor both based on thermal conductivity measurement.

These and other features and advantages of the invention will be apparent to those skilled in the art from the following detailed description of preferred embodiments, taken together with the accompanying drawings.

BRIEF DESCRIPTION OF THE DRAWINGS

The exemplary embodiment(s) of the present invention will be understood more fully from the detailed description given below and from the accompanying drawings of various embodiments of the invention, which, however, should not be taken to limit the invention to the specific embodiments, but are for explanation and understanding only.

FIG. 6 to FIG. 7A illustrates the top-plane views of the single silicon wafer micromachined thermal conduction sensor of FIG. 1 at 6 to 7 stages in the fabrication thereof.

FIG. 7B to FIG. 8 illustrates the cross-sectional views of the single silicon wafer micromachined thermal conduction sensor of FIG. 1 at 8 to 9 stages in the fabrication thereof.

DETAILED DESCRIPTION

Figure 1:
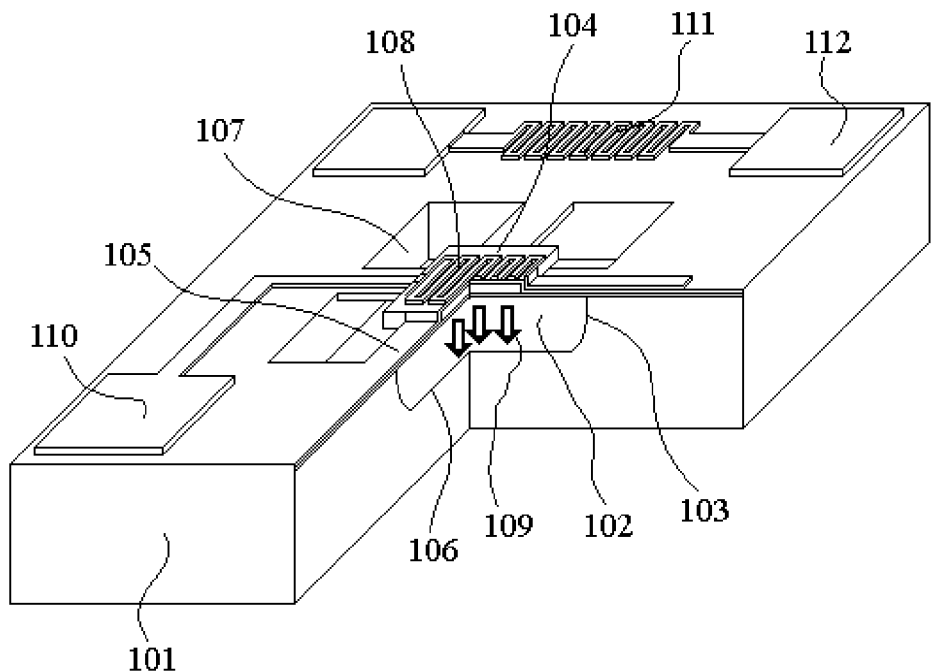
FIG. 1 illustrates the perspective, partially cross-sectional, diagrammatic sketch of a single silicon wafer micromachined thermal conduction sensor in accordance with the present invention.

In order to achieve the above objects, referring to FIG. 1, a single silicon wafer micromachined thermal conduction sensor consists of a heat transfer cavity 102 having a flat bottom and an arbitrary plane shape, which is all created in a silicon substrate 101 and in which heat transfer is through gas thermal conduction in one direction, as shown by arrows 109, a frame 103 resulted by creating the cavity 102 and having a curved wall supporting and surrounding the cavity 102, a thin film bridge 104 suspending over the cavity 102 and having a central wide section and two side narrow sections 105 on the two opposite sides of the central wide section, which is arranged in a line and extending to the edge of the frame 103, a heated resistor 108 disposed on the surface of the central wide section of the bridge 104, a heat sink 106 being the flat bottom of the cavity 102 and parallel to the bridge 104, a temperature sensors 111 disposed on the surface of the frame 103, at least one openings 107 disposed between the bridge 104 and frame 103 and used for the cavity 102 to communicate with the outside, four bonding pads 110 and 112 are disposed near the edge of the surface of the substrate 101, which electrically connect the heated resistor 108 and the temperature sensor 111 to an outside circuit.

It should be emphasized that the gap of the heat transfer cavity 102 is restricted in the range of 5 to 50 microns. In this case no natural convection takes place completely in the cavity. The heat transfer from the heated resistor 108 to the heat sink 106 is through the gas thermal conduction in the cavity along the vertical direction, as shown by arrows 109 in FIG. 1.

It should be understood that in fluid dynamics and heat transfer Grashof number approximates the ratio of the buoyancy to viscous force acting on a fluid. For an enclosed cavity Grashof number can be expressed by $G_{rL}=g\beta(T_h-T_c)L^3/v^2$, where L=cell depth, g=acceleration due to gravity, $T_h$=temperature of heat source, $T_c$=temperature of heat sink, v=Kinematic viscosity (for air, $v=20.94\times10^{-6}$ (m$^2$/s), β=Thermal expansion coefficient (for air, $\beta=2.83\times10^{-3}$). Assuming that the cavity 102 is filled with air, the temperature different between the heated resistor 108 and the heat sink 106 is 200° C., the gap of the cavity is 50 microns, it can be calculated that the Grashof number is $1.581\times10^{-3}$. Such small Grashof number means that in the cavity the heat transfer of one dimensional conduction overwhelmingly prevails over natural convection.

It is necessary to be noted that the heat transfer cavity 102 may take an arbitrary plane shape. It is preferred to be square or circle, but not limited to these two shapes. The side length of the square shape may be chosen in the range from 400 to 2000 microns. The diameter of the circle shape may be chosen in the range from 400 to 2000 microns.

It is preferred that the bridge 104 consists of SiO$_2$/Si$_3$N$_4$ double layers. As well known, a silicon nitride layer and a silicon oxide layer deposited on a silicon wafer possess compressive and tensile intrinsic stresses, respectively. The combination of nitride/oxide double layers with the opposite stresses led to a lower residual tensile stress.

As an alternative, the bridge 104 consists of Si$_3$N$_4$/polysilicon/Si$_3$N$_4$ sandwiched layers. The residual stress in an as-LPCVD-deposited polysilicon layer is compressive, which can be used to offset the tensile stress of the silicon nitride layer. In addition, the polysilicon layer sandwiched between the two silicon nitride layers may uniform the temperature distribution of the bridge 104, because polysilicon possess higher a thermal conductivity than silicon nitride.

Preferably, the bridge 104 has a central wide section and two side narrow sections, which are arranged in a line and extend to the edge of the frame 103 and has a length ranging from 200 to 800 microns and a thickness ranging from 1 to 3 microns.

Preferably, the heated resistor 108 and the temperature sensor 110 are made of Nickel or Platinum in order to obtain a temperature dependence resistance. The heated resistor 108 is disposed on the surface of the central wide section of the bridge 104 and may be arranged in zigzag shape in order to obtain an appropriate resistance. The temperature sensor 110 is disposed on the surface of the silicon frame 103 and may also be arranged in zigzag shape.

The goal of the design of the thermal conduction sensor is to simply the temperature behavior of the heated resistor such that it may be described by one dimensional mathematical model. In this model, the following assumptions should be true: the bridge 104 carrying the heated resistor 108 and the heat sink 107 are parallel, and the thickness of the bridge 104 is much smaller than its length; all the heat generated by the heated resistor 108 is transferred to the heat sink 107 by thermal conduction through the gas filled in the cavity 102; the gap of the cavity 102 and the temperature of the heated area by the resistor 108 are uniform and consistency. Based on one dimensional mathematical model, the thermal conduction sensor can be used in the analysis of mixtures gas composition, such as natural gas consisting of methane, hydrocarbons, carbon dioxide and nitrogen. Obviously, the thermal conduction sensor can also be used as a thermal conductivity vacuum sensor and a thermal conductivity humidity sensor without any changes.

Referring in more detail to FIG. 2 through FIG. 8, the method of fabricating the single silicon wafer micromachined thermal conduction sensor in accordance with the present invention will be described.

The thermal conduction sensor is fabricated using a silicon substrate as a starting material. The crystal orientation and the resistivity of the silicon substrate are $p^+$-type (100) and in the range of 0.1 to 0.001 ohm-cm, respectively.

Figure 2:
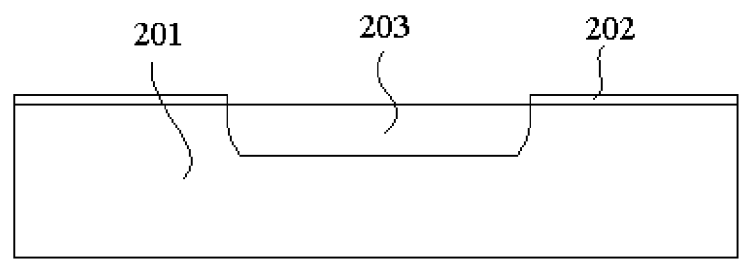
FIG. 2 to FIG. 5 illustrates the cross-sectional views of the single silicon wafer micromachined thermal conduction sensor of FIG. 1 at 1 to 4 stages in the fabrication thereof. The sensor is preferably fabricated using standard silicon processing techniques (photolithography, Thermal diffusion, LPCVD, wet and dry etching etc.).

As shown in FIG. 2, the first fabrication step of the sensor is to deposit a silicon nitride layer on the surface of the substrate 201 by LPCVD (low pressure chemical vapor deposition). The thickness of the silicon nitride layer is chosen in the range between 1500 to 3000 Angstroms. A photolithography process is performed to create an anodization mask 202 through partially etching the silicon nitride layer. The etching of the silicon nitride is carried out by dry etching. A resulted transparent window in the silicon nitride layer is a square shape with a side length ranging from 400 to 2000 microns. It should be noted that the resulted transparent window is not limited to square shape. It may be an arbitrary shape including a circle shape with a diameter ranging from 400 to 2000 microns.

Figure 3:
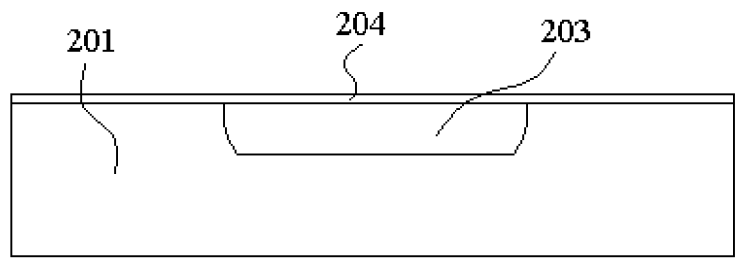

The second fabrication step is to conduct the anodization of the silicon substrate 201 in a HF solution, as shown in FIG. 3. An anodization cell to be used is made of Teflon and divided into two compartments by the silicon substrate to be anodized. Each compartment has a platinum electrode with its distal end connecting to a power supply. A HF solution to be used is a mixer of 1 or 2 part 48 wt % HF and 1 part ethanol. The anodic current is chosen in the range from 40 to 80 mA/cm.sup.2, which is kept constant during the anodization. The formed porous silicon has a porosity of about 50 to 70%. It can be seen that the anodization is restricted in the square region and only to convert the upper layer of the silicon substrate 201 into porous silicon layer 203, which has a thickness in the range of 5 to 50 microns. The porous silicon layer 203 is subjected to a post thermal treatment for stabilizing porous structure. The thermal treatment is performed at 400.degree Celsius in dry oxygen for 30 min. As a result, one or two atom layer thick silicon dioxide film is formed on the surface of the inner pores of the porous silicon, which can stabilize the porous structure of the porous silicon layer 203.

Figure 4:
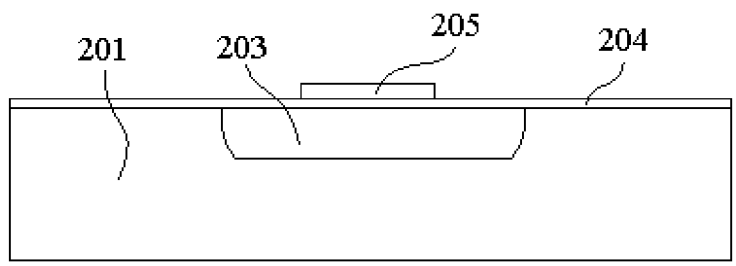

After removing the residual silicon nitride layer the third fabrication step is to follow. This step is to deposit a first insulating layer 204 consisting of silicon nitride on the surface of the silicon substrate 201 including the surface of the porous silicon layer 203, as shown in FIG. 4. The thickness of the silicon nitride layer is in the range of 1500 to 3000 Angstroms. The deposition of silicon nitride is conducted by LPCVD process. Clearly, the insulating film 205 can be used to seal the pores of the porous silicon layer 203 so as to prevent the porous silicon layer from degenerate.

Figure 5:
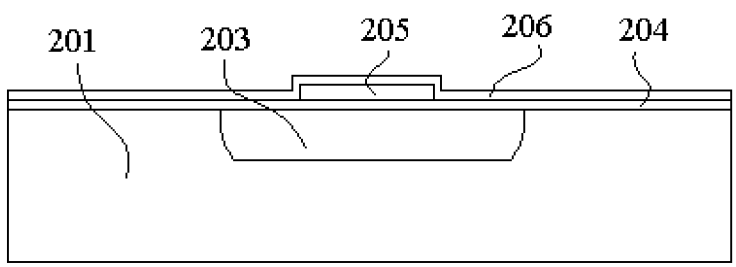

As shown in FIG. 5, the fourth fabrication step is for creating a polysilicon block 205. To do this, a polysilicon layer is first deposited on the surface of the insulating layer 204 by LPCVD. The thickness of the polysilicon layer may be 1 to 4 microns. After a photolithography process a part of the polysilicon layer is etched away by dry etching. As a result, the polysilicon block 205 is formed, beneath which there is the porous silicon layer 203.

The fifth fabrication step is to deposit a second insulating layer 206 consisting of silicon nitride layer on the surface of the substrate 201 including the surface of the polysilicon block 205 by LPCVD. The thickness of the insulating film 206 is in the range from 1500 to 3000 Angstroms. It can be seen that the second insulating film 206 combines the first insulating layer 204 to form a composite insulating layer around the polysilicon block 205.

Figure 6:
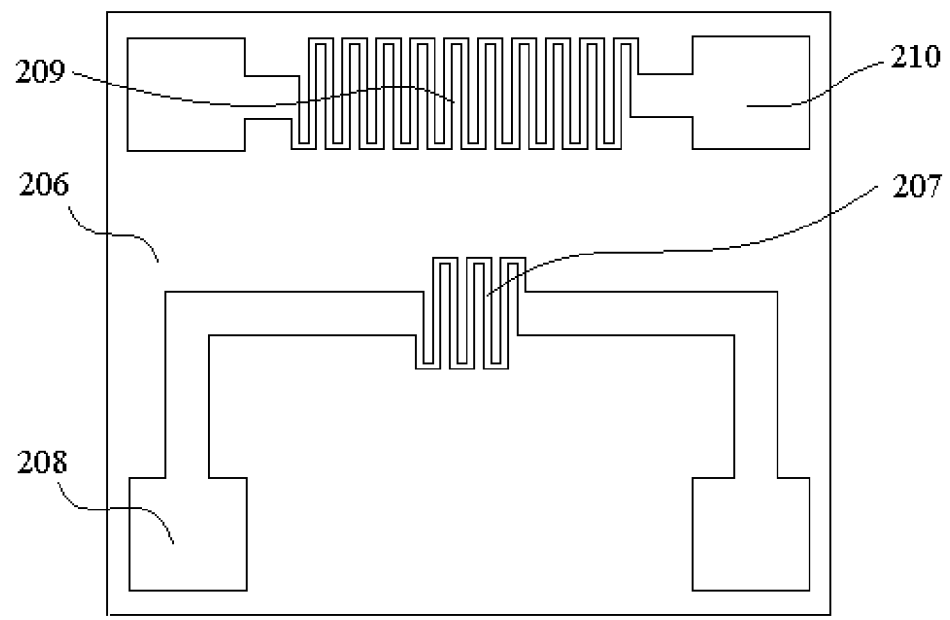

The sixth fabrication step is to build a heated resistor 207, a temperature sensor 209 and four bonding pads 208 and 210 on the surface of the second insulating layer 206. It is preferred that the heated resistor 207 and temperature sensor 209 are made of platinum and formed by a lift-off process. The lift-off process consists of the following steps. First, a pattern of positive photoresist is created by a photoresist process. Secondly, a platinum layer is deposited over the photoresist pattern by electron beam evaporation or sputtering. Thirdly, the pattern of positive photoresist is removed by immerse in acetone solution. As shown in FIG. 6 the resulted platinum resistors are arranged in zigzag shape. The thickness of the platinum layer is in the range of 1000 to 3000 Angstroms and the resistance of the platinum resistors is in the range of 50 to 1000 ohm.

As an alternative, the heated resistor 207 and temperature sensor 209 are made of nickel. Since nickel can be etched by wet etching nickel pattern can be created on the surface of the silicon substrate 201 without using lift-off process.

It should be noted that the silicon substrate with the photoresist pattern is not be allowed to heat beyond 150.degree censes during the lift-off process. This is to ensure that the photoresist is not harmed so that it is easy to remove by immersion in acetone. The lift-off process results a pattern consisting of a heated resistor 207, two bonding pads 208 for the heated resistor 207, a temperature sensor 209, and two bonding pads 210 for the temperature sensor 209, as shown in FIG. 5. Generally, the platinum pattern deposited by sputtering needs to be annealing at 500 degree censes in nitrogen for 30 min before performing the next fabrication step.

As shown in FIG. 7B, the seventh fabrication step is to form 4000 Angstroms thick amorphous silicon carbide film 213 protecting the surface of the substrate including the surface of the platinum pattern by PECVD. Then a photolithography process is performed to reveal the bonding pads 208 and 210. The unwanted amorphous silicon carbide is removed by dry etching.

Figure 7A:
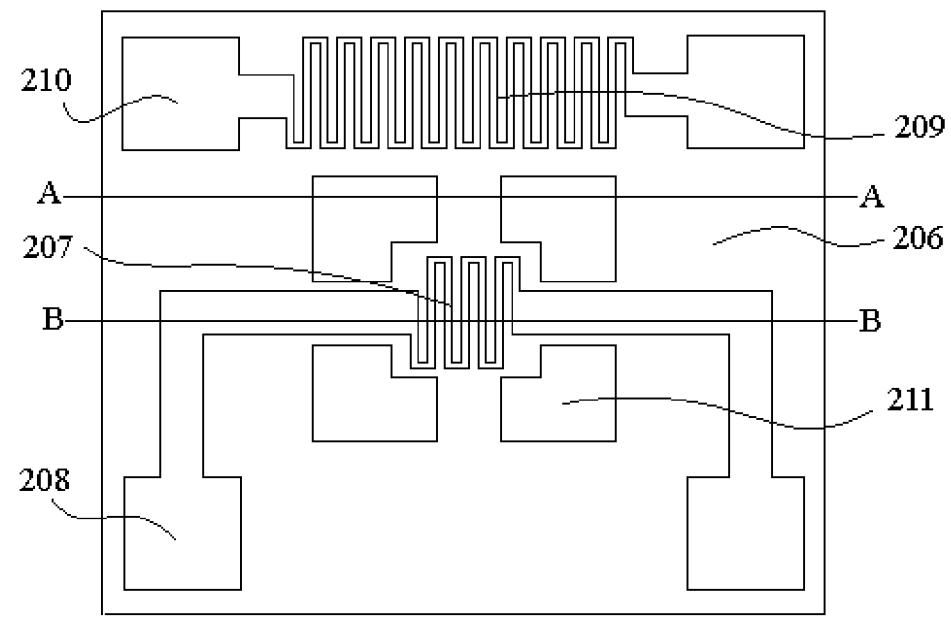

As shown in FIG. 7A, the eighth fabrication step is to create openings 214 in the first insulating film 204 and the second insulating film 206 around the polysilicon block 205. This is done by forming a photoresist pattern and then dry etching the insulating film using the photoresist pattern as a etch mask.

Figure 8:
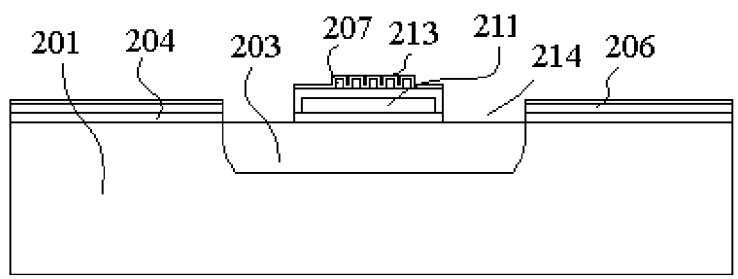
Figure 8:
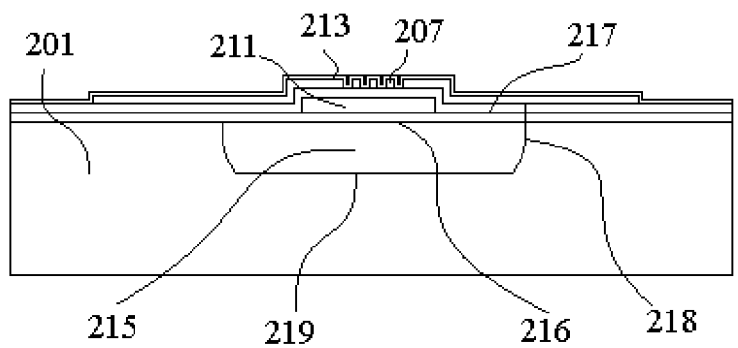

The ninth fabrication step is to etch away the porous silicon in the openings and under the polysilicon block. The etchant to be used is a KOH solution of 1-3 w %. The etchant cannot attack the porous silicon layer immediately since the surface of the inner pores of the porous silicon is coated with a thin silicon nitride film or silicon dioxide film. The etchant also can not attack the silicon of the silicon substrate since the KOH solution is diluted and the etching is performed at room temperature. After the etching, a heat transfer cavity 215, a thin film bridge 216 being the top of the cavity 215, four side narrow sections 217 supporting the central wide section of the bridge 216, a frame 218 surrounding the cavity 215, and a heat sink 219 being the flat bottom of the cavity 215 are formed, as shown in FIG. 8.

Other embodiments are within the spirit and scope of the appended claims. Numerous variations and alternate embodiments will occur to those skilled in the art without departing from the spirit and scope of the invention.

While the present invention has been described with reference to particular embodiment(s) of the silicon wafer micromachined thermal conduction sensor, it is obvious that other embodiments can be used without departing from the teachings herein. Obviously, many modifications and variations are possible in light of the teaching herein. It is therefore to be understood that within the scope of the appended claims, the present invention may be practiced other than as specifically described.

What is claimed is:

1. A single silicon wafer micromachined thermal conduction sensor comprising:
   a heat transfer cavity having a flat bottom and a plane shape, which is created in a silicon substrate,
   a frame resulted by creating the cavity in the substrate and having a curved side wall supporting and surrounding the cavity,
   a thin film bridge suspending over the cavity and extending to the edge of the frame, which has a wide central section and at least two side narrow sections on the two opposite sides of the central section,
   a heated resistor disposed at the surface of the central section of the bridge, which has a temperature dependence resistance,
   a heat sink being the flat bottom of the cavity and parallel to the bridge, and
   a temperature sensor disposed on the surface of the frame.

2. The single silicon wafer micromachined thermal conduction sensor as recited in claim 1, wherein said heat transfer cavity has a square plane shape with a side length ranging from 400 to 2000 microns.

3. The single silicon wafer micromachined thermal conduction sensor as recited in claim 1, wherein said heat transfer cavity has a circle plane shape with a diameter ranging from 400 to 2000 microns.

4. The single silicon wafer micromachined thermal conduction sensor as recited in claim 1, wherein said heat transfer cavity has a vertical distance or gap between the bridge and the bottom, which is in the range from 5 to 50 microns.

5. The single silicon wafer micromachined thermal conduction sensor as recited in claim 4, wherein said temperature sensor is made of Nickel or Platinum and has a resistance ranging from 50 to 1000 ohm.

6. The single silicon wafer micromachined thermal conduction sensor as recited in claim 1, wherein said central section of the bridge is a thin film structure consisting of $SiO_2/Si_3N_4$ or $Si_3N_4/polysilicon/Si_3N_4$ and has a square shape with a side length ranging from 200 to 1000 microns and a thickness ranging from 1 to 3 microns.

7. The single silicon wafer micromachined thermal conduction sensor as recited in claim 1, wherein said side sections of the bride are thin film structure consisting of $SiO_2/Si_3N_4$ and has a length ranging from 200 to 1000 microns, a width ranging from 10 to 100 microns and a thickness ranging from 2000 to 8000 Angstroms.

8. The single silicon wafer micromachined thermal conduction sensor as recited in claim 1, wherein said heated resistor is made of Nickel or Platinum and has a resistance ranging from 50 to 1000 ohm.

* * * * *